United States Patent [19]
Emerit

[11] Patent Number: 5,984,876
[45] Date of Patent: Nov. 16, 1999

[54] SUCTION SYRINGE AND SUCTION DEVICE COMPRISING SAME

[76] Inventor: Michel Emerit, 33 rue d'Alsace 95110, Sannois, France

[21] Appl. No.: 09/051,875
[22] PCT Filed: Oct. 16, 1996
[86] PCT No.: PCT/FR96/01623
  § 371 Date: Apr. 16, 1998
  § 102(e) Date: Apr. 16, 1998
[87] PCT Pub. No.: WO97/14452
  PCT Pub. Date: Apr. 24, 1997

[30] Foreign Application Priority Data

Oct. 17, 1995 [FR] France .................................. 95 12161

[51] Int. Cl.⁶ ............................................. A61B 5/103
[52] U.S. Cl. ........................................ 600/578; 604/315
[58] Field of Search .................................. 600/573, 578; 604/313, 315, 312, 289, 290

[56] References Cited

U.S. PATENT DOCUMENTS 4,116,240  9/1978  Guiney .
5,095,914  3/1992  Sarstedt ................................... 600/578
5,871,456  2/1999  Armstrong et al. .................... 604/316

FOREIGN PATENT DOCUMENTS

| | | |
|---|---|---|
| 0 208 975 | 1/1987 | European Pat. Off. . |
| 2 554 002 | 5/1985 | France . |
| 2 574 299 | 6/1986 | France . |
| 2 626 179 | 7/1989 | France . |
| 2 008 200 | 5/1979 | United Kingdom . |
| 86/04819 | 8/1986 | WIPO . |

*Primary Examiner*—Max Hindenburg
*Attorney, Agent, or Firm*—Wenderoth, Lind & Ponack, L.L.P.

[57] ABSTRACT

A disposable suction syringe consists of three parts, i.e. a tubular body (1) defining an inwardly smooth barrel (4) with one open end (5) and a bottom wall (6) at the other end, and further comprising two gripping flanges (11); an assembly of a solid rod (12) and a plunger (14), wherein the rod extends through a converging sealing lip (7) projecting outwards from said bottom wall, while the plunger (14) comprises a diverging sealing skirt (15) extending away from said wall; and an actuating button (3) attached to the proximal end of the rod (12). The syringe may be used by a person to suck venom out of his or her own body.

23 Claims, 2 Drawing Sheets

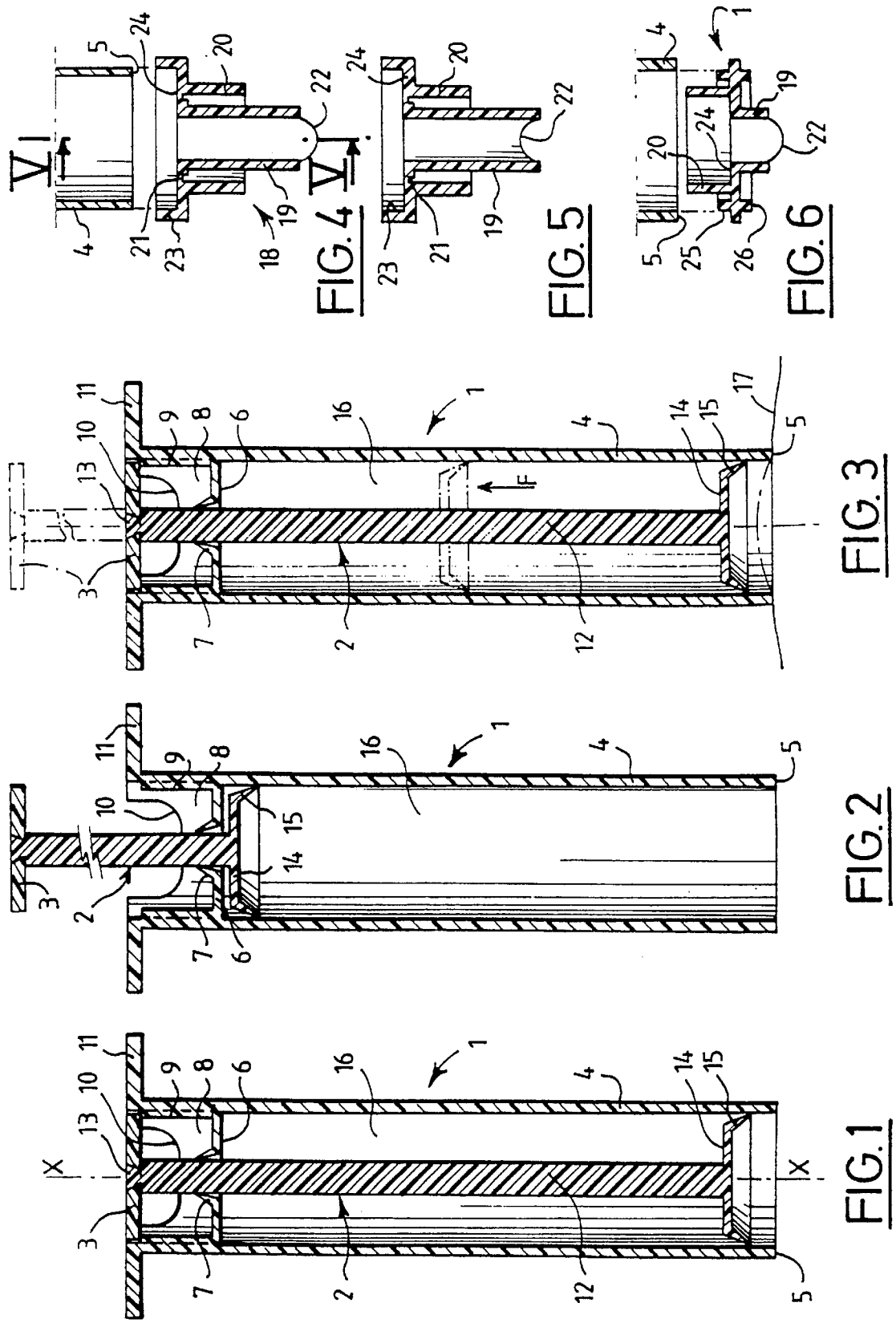

SUCTION SYRINGE AND SUCTION DEVICE COMPRISING SAME

BACKGROUND OF THE INVENTION

The present invention concerns an aspirator syringe.

Aspirator syringes intended for self-use to suck out venom from a bite or a sting are described in FR-A-2 408 738.

The above syringes have been a considerable commercial success but are relatively sophisticated devices incorporating a large number of parts and relatively costly to manufacture.

SUMMARY OF THE INVENTION

An aim of the invention is to provide a much more economical aspirator syringe designed to be discarded after use.

To this end the aspirator syringe in accordance with the invention consists of three parts including: a tubular plastic body defining over most of its length a sleeve open at one end and having an end wall at the other end, the sleeve having a smooth inside wall, the end wall having a central orifice delimited by a convergent annular lip directed axially towards the exterior of the sleeve, the body having two holding lugs projecting radially outwards; a plastic piston rod/piston assembly including a piston rod that is solid or has no through conduit therein and that passes through the orifice in the end wall and cooperates with the annular lip to form a seal, and a piston at the distal end of the piston rod having a divergent peripheral skirt directed towards the open end of the sleeve and cooperating in sealed manner with the smooth inside wall of the sleeve; and an actuator button fixed to the proximal end of the piston rod.

Further aspects of the invention include the following. The body one has an abutment with which the button comes into contact when the skirt of the piston is near the open end of the sleeve and is in contact with the smooth inside wall of the sleeve. The body has at its proximal end beyond the end wall an extension which defines two diametrically opposed notches. A proximal end part of the piston rod has a smaller cross-section than other parts of the piston rod, and the body includes relative locating means which locate the proximal end of the piston rod in line with the lip of the end wall without contact therewith. The button and the body may include relative locating means which locate the end of the skirt of the piston beyond the open end of the sleeve or facing an internal opening in the sleeve and without contact with the sleeve. The relative locating means may include a recess in the body nearer the end wall than the abutment means and a tooth that prevents the button from returning to the recess after it has moved beyond the abutment means.

The present invention also contemplates an aspirator device comprising an aspirator syringe consisting of three parts including a tubular plastic body, a piston rod/piston assembly and an actuator button, as described above, and the aspirator device further including at least one plastic nozzle adapted to fit over or in and to be sealed to the open end of the sleeve of the syringe.

Further aspects of the aspirator device include the following. The nozzle may include two aspirator conduits with different configurations and means for selecting one or the other of the conduits. The two conduits may project from the distal end of the nozzle, and at least one of the two conduits is adapted to be eliminated by means of a fragile area connecting it to the remainder of the nozzle. The two conduits may project from respective opposite ends of the nozzle which include means adapted to fit over or into the open end of the sleeve in one direction or the other. The at least one plastic nozzle may comprise at least two interchangeable nozzles having different aspiration configurations.

BRIEF DESCRIPTION OF THE DRAWINGS

Embodiments of the invention will now be described with reference to the appended drawings, in which:

FIG. 1 is a longitudinal sectional view of an aspirator syringe in accordance with the invention in a storage configuration;

FIG. 2 is a similar view showing the first phase of use of the syringe;

FIG. 3 is a similar view showing the second phase of use of the syringe;

FIG. 4 shows in longitudinal section a nozzle adapted to be fitted to the aspirator syringe from FIGS. 1 through 3;

FIG. 5 is a view of the same nozzle in section taken along the line V—V in FIG. 4;

FIG. 6 is a view similar to FIG. 4 of a variant nozzle; and

DETAILED DESCRIPTION OF THE INVENTION

Figure 9:
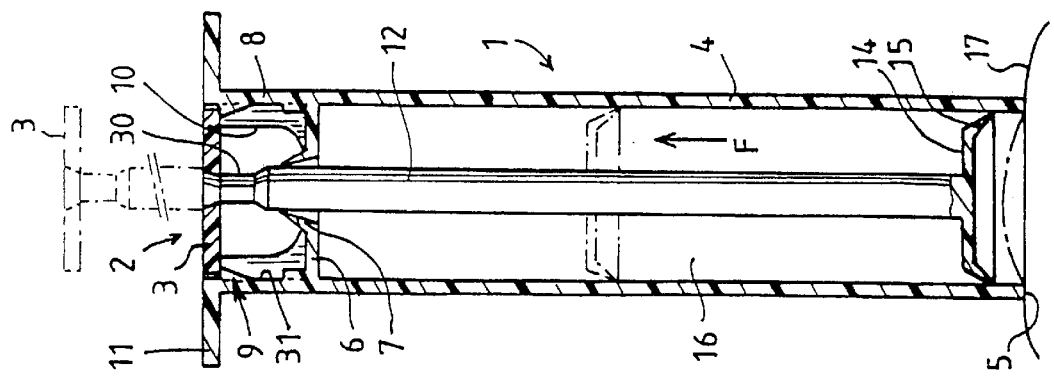
FIGS. 7 through 9 are views respectively similar to FIGS. 1 through 3 but relating to a variant of the syringe.

The aspirator syringe shown in FIG. 1 consists in three parts moulded from plastic material, namely a tubular body 1, a piston rod/piston assembly 2 and an actuator knob (or button) 3.

Over most of its length the tubular body 1 forms a circular section cylindrical sleeve 4 of constant wall thickness, internally smooth throughout its length and open at its distal end to define a planar circular end face 5. For convenience of description, the syringe will be deemed to be oriented as shown, that is to say with its main axis X-vertical and its distal end at the bottom.

The sleeve 4 has a horizontal end wall 6 at its top end. This end wall includes a central orifice delimited by a convergent upwardly projecting annular lip 7.

Above the end wall 6 the sleeve 4 is extended by a top collar 8 with the same section having two diametrically opposed vertical ribs 9 on its inside surface ending at a small distance from the upper end of the collar. The collar 8 also has two notches 10 at 90° to the above ribs and two holding lugs 11 in line with the ribs that project radially outwards. The lugs are horizontal and flush with the upper end of the collar 8.

The piston rod/piston assembly 2 comprises a solid rod 12 which passes in a sealed manner through the lip 7 and carries a snap-fastener stud 13 at its upper end. The lower end of the piston rod forms a flat piston 14 which has a downwardly facing divergent skirt 15 at its periphery. The piston rod 12 cooperates with the lip 7 in a sealed manner and the skirt 15 cooperates with the smooth inside wall of the sleeve 4 in the sealed manner.

The button 3 is flat and horizontal and has a central orifice which snaps over the stud 13 on the piston rod 12.

When the syringe is assembled the piston rod 12 is inserted into the body 1 from below, through the lip 7, which rubs on it, and is pushed upwards until the skirt 15 is entirely within the sleeve 4. The stud 13 is then almost level with the lugs 11 and the button 3 is clipped onto the stud. Its periphery then rests on the upper end of the ribs 9 and the upper face of the button is flush with that of the lugs 11.

In this storage configuration the pressure in the annular chamber 16 delimited by the sleeve 4, the end wall 6, the piston rod 12 and the piston 14 is substantially equal to atmospheric pressure.

To use the syringe, the body 1 is grasped in one hand, two fingers are inserted in the notches 10 and the button 3 is raised. This pulls up the assembly 2–3 and the air contained in the chamber 16 is expelled by the lip 7 lifting elastically off the piston rod 12 and the skirt 15 lifting elastically off the sleeve 4.

This leads to the stable configuration shown in FIG. 2 in which the piston 14 is just below the end wall 6.

The remainder of use of the syringe is effected with only one hand: it is grasped with two fingers under the lugs 11 and the thumb on the button 3 and the latter is pushed down.

During this movement the lip 7 and the skirt 15 provide a seal in the manner of a valve so that the pressure in the chamber 16 falls progressively to a minimum when the assembly 2–3 returns to its initial position defined by the button 3 abutting on the ribs 9.

The configurations of FIGS. 1 and 3 differ in terms of the pressure in the chamber 16, however.

The lower end face 5 is then pressed onto the skin 17 around the sting or the bite (FIG. 3) and the button 3 is released. Because of the reduced pressure in the chamber 16, the piston 14 rises of its own accord (arrow F) which reduces the pressure between the piston and the skin. The latter is therefore aspirated upwards, as shown in chain-dotted line in FIG. 3, which removes the venom.

Note that the face 5 can be removed from the skin, if necessary, the button pushed in again and the face 5 applied to the skin again to reinforce the aspiration effect. However, it is normally not possible to re-establish atmospheric pressure in the chamber 16, with the result that the syringe must in principle be discarded after use.

The syringe can be provided with a set of interchangeable nozzles that fit over or into the lower end of the sleeve 4. In one variant, as shown in FIGS. 4 and 5 at least one nozzle 18 with two concentric conduits 19 and 20 can be used, and the longer conduit, which is the inner conduit 19 in this example, can be removed by breaking a fragile area 21 at its base. In this example the conduit 19 has a saddle-shaped free end 22 adapted to fit the shape of the finger, in particular the finger of a child.

The nozzle 18 fits over and is sealed to the lower end of the sleeve 4 by means of a slightly divergent top collar 23 bordering the periphery of its end wall 24. In the FIG. 6 variant, on the other hand, the nozzle fits into and is sealed to this lower end by means of a slightly convergent top collar 25 offset radially form the periphery of the end wall 24.

In the FIG. 6 variant there is a second collar 26 symmetrical to the collar 25 about the end wall 24 and the aspirator conduits 19 and 20 project from this end wall, one downwards and the other upwards.

Figure 7:
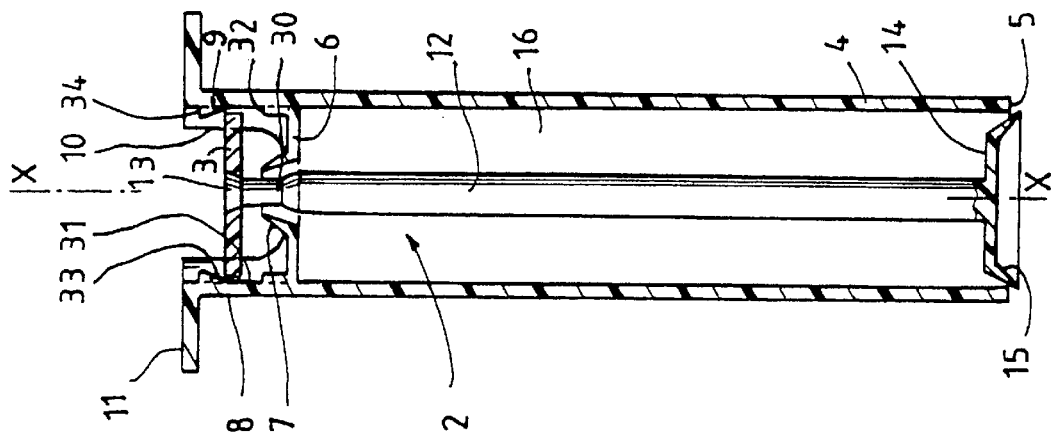

The variant of the syringe shown in FIGS. 7 through 9 differs from the previous one in the following respects.

On the one hand, the upper part 30 of the piston rod 12, immediately under the button 3, has a smaller diameter.

On the other hand, each rib 9 has at an intermediate level a recess 31 delimited at the bottom by a horizontal face 32 and at the top by a ramp 33 which converges in the upward direction. The latter merges with the horizontal top end face 34 of the rib 9 so as to form a tooth.

In the storage configuration of the syringe (FIG. 7) the button 3 is in the recess 31. This brings the narrower section 30 of the piston rod 12 into line with the lip 7 and the free end of the skirt 15 beyond the lower end 5 of the body 1. Consequently the two seals 7, 15 remain effective even after long storage.

To use the syringe the operator slips two fingers under the button 3 through the notches 10 and raises the button. The elasticity of the collar 8 and the ramps 33 then allow the button to move above the ribs 9.

Figure 8:
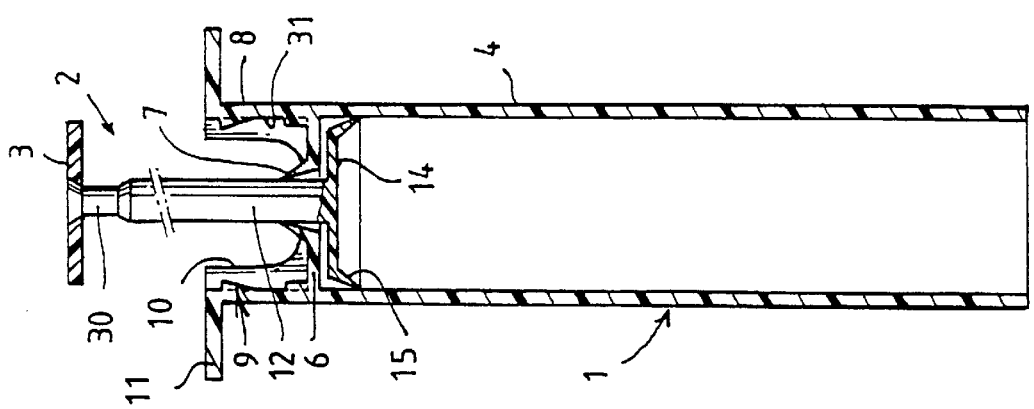

Then, as described above with reference to FIGS. 2 and 3, the button 3-piston rod 12 assembly is pulled upwards as far as possible (FIG. 8). At the beginning of this movement the seals 7 and 15 are deformed by the piston rod 12 and by the sleeve 4, respectively.

The button 3 is then pressed in again (FIG. 9) to create the vacuum in the body 1. This movement is stopped positively by the button 3 abutting on the top faces 34 of the ribs 9 with the result that the seal is maintained permanently at the level of the two seals.

In a variant the lip 15 could be aligned in the storage configuration with an interior recess in the sleeve 4 without any contact therewith.

I claim:

1. An aspirator syringe consisting of three parts including:
   (a) a plastic tubular body (1) defining over most of its length a sleeve (4) open at one end (5) and having an end wall (6) at the other end, said sleeve having a smooth inside wall, the end wall having a central orifice delimited by a convergent annular lip (7) directed axially towards the exterior of the sleeve, the body (1) having two holding lugs (11) projecting radially outwards;
   (b) a plastic piston rod/piston assembly (2) including a piston rod (12) that is solid or has no through conduit therein and that passes through the orifice in said end wall (6) and cooperates with the annular lip (7) to form a seal, and a piston (14) at the distal end of the piston rod having a divergent peripheral skirt (15) directed towards the open end of the sleeve (4) and cooperating in sealed manner with said smooth inside wall of the sleeve; and
   (c) an actuator button (3) fixed to the proximal end of the piston rod (12);
   wherein the body (1) has an abutment (9) with which the button (3) comes into contact when the skirt (15) of the piston (14) is near the open end (5) of the sleeve (4) and is in contact with said smooth inside wall of the sleeve.

2. An aspirator syringe according to claim 1 characterised in that a proximal end part (30) of the piston rod (12) has a smaller cross-section than other parts of the piston rod and in that the button (3) and the body (1) include relative locating means (31) which locate the proximal end part of the piston rod in line with the lip (7) of the end wall (6) without contact therewith.

3. An aspirator syringe according to claim 1 characterised in that the button (3) and the body (1) include relative locating means (31) which locate the end of the skirt (15) of the piston (14) beyond the open end of the sleeve (4) or facing an internal opening in the sleeve and without contact with the sleeve.

4. An aspirator syringe according to claim 1 characterised in that a proximal end part (30) of the piston rod (12) has a smaller cross-section than other parts of the piston rod, in that the button (3) and the body (1) include relative locating means (31) which locate the proximal end part of the piston rod in line with the lip (7) of the end wall (6) without contact therewith and in that the relative locating means (31) include a recess in the body (1) nearer the end wall (6) than said abutment means (9) and a tooth (33–34) that prevents the button (3) from returning to the recess (31) after it has moved beyond said abutment means (9).

5. An aspirator syringe according to claim 1 characterised in that the button (3) and the body (1) include relative locating means (31) which locate the end of the skirt (15) of the piston (14) beyond the open end of the sleeve (4) or facing an internal recess in the sleeve and without contact therewith and in that the relative locating means (31) comprise a recess in the body (1) nearer the end wall (6) than said abutment means (9) and a tooth (33–34) that prevents the button (3) from returning to the recess (31) after it has moved beyond said abutment means (9).

6. An aspirator syringe according to claim 1 characterized in that the body (1) has at its proximal end beyond the end wall (6) an extension (8) which defines two diametrically opposed notches (10).

7. An aspirator syringe consisting of three parts including:
   (a) a plastic tubular body (1) defining over most of its length a sleeve (4) open at one end (5) and having an end wall (6) at the other end, said sleeve having a smooth inside wall, the end wall having a central orifice delimited by a convergent annular lip (7) directed axially towards the exterior of the sleeve, the body (1) having two holding lugs (11) protecting radially outwards;
   (b) a plastic piston rod/piston assembly (2) including a piston rod (12) that is solid or has no through conduit therein and that passes through the orifice in said end wall (6) and cooperates with the annular lip (7) to form a seal, and a piston (14) at the distal end of the piston rod having a divergent peripheral skirt (15) directed towards the open end of the sleeve (4) and cooperating in sealed manner with said smooth inside wall of the sleeve; and
   (c) an actuator button (3) fixed to the proximal end of the piston rod (12);
   wherein the body (1) has at its proximal end beyond the end wall (6) an extension (8) which defines two diametrically opposed notches (10).

8. An aspirator device comprising:
   an aspirator syringe (1–3) consisting of three parts including
   (a) a plastic tubular body (1) defining over most of its length a sleeve (4) open at one end (5) and having an end wall (6) at the other end, said sleeve having a smooth inside wall, the end wall having a central orifice delimited by a convergent annular lip (7) directed axially towards the exterior of the sleeve, the body (1) having two holding lugs (11) projecting radially outwards,
   (b) a plastic piston rod/piston assembly (2) including a piston rod (12) that is solid or has no through conduit therein and that passes through the orifice in said end wall (6) and cooperates with the annular lip (7) to form a seal and a piston (14) at the distal end of the piston rod having a divergent peripheral skirt (15) directed towards the open end of the sleeve (4) and cooperating in sealed manner with said smooth inside wall of the sleeve, and
   (c) an actuator button (3) fixed to the proximal end of the piston rod (12); and
   at least one plastic nozzle (18) adapted to fit over or in and to be sealed to the open end of the sleeve (4) of the syringe,
   wherein the body (1) has an abutment (9) with which the button (3) comes into contact when the skirt (15) of the piston (14) is near the open end (5) of the sleeve (4) and is in contact with said smooth inside wall of the sleeve.

9. An aspirator device according to claim 8 characterised in that the nozzle (18) includes two aspirator conduits (19, 20) with different configurations and means (21; 25, 26) for selecting one or the other of said conduits.

10. An aspirator device according to claim 9 characterised in that the two conduits (19, 20) project from the distal end of the nozzle (18), at least one of the two conduits being adapted to be eliminated by means of a fragile area (21) connecting it to the remainder of the nozzle.

11. An aspirator device according to claim 9 characterised in that the two conduits (19, 20) project from respective opposite ends of the nozzle (18) which includes means (25, 26) adapted to fit over or into the open end (5) of the sleeve (4) in one direction or the other.

12. An aspirator device according to claim 8 wherein the at least one plastic nozzle comprises at least two interchangeable nozzles having different aspiration configurations.

13. An aspirator syringe comprising three parts including:
   (a) a plastic tubular body (1) defining over most of its length a sleeve (4) open at one end (5) and having an end wall (6) at the other end, said sleeve having a smooth inside wall, the end wall having a central orifice delimited by a convergent annular lip (7) directed axially towards the exterior of the sleeve, the body (1) having two holding lugs (11) projecting radially outwards;
   (b) a plastic piston rod/piston assembly (2) including a piston rod (12) that is solid or has no through conduit therein and that passes through the orifice in said end wall (6) and cooperates with the annular lip (7) to form a seal, and a piston (14) at the distal end of the piston rod having a divergent peripheral skirt (15) directed towards the open end of the sleeve (4) and cooperating in a sealed manner with said smooth inside wall of the sleeve; and
   (c) an actuator button (3) fixed to the proximal end of the piston rod (12);
   wherein the body (1) has an abutment (9) with which the button (3) comes into contact when the skirt (15) of the piston (14) is near the open end (5) of the sleeve (4) and is in contact with said smooth inside wall of the sleeve.

14. An aspirator syringe according to claim 13 characterised in that a proximal end part (30) of the piston rod (12) has a smaller cross-section than other parts of the piston rod and in that the button (3) and the body (1) include relative locating means (31) which locate the proximal end part of the piston rod in line with the lip (7) of the end wall (6) without contact therewith.

15. An aspirator syringe according to claim 13 characterised in that the button (3) and the body (1) include relative locating means (31) which locate the end of the skirt (15) of the piston (14) beyond the open end of the sleeve (4) or facing an internal opening in the sleeve and without contact with the sleeve.

16. An aspirator syringe according to claim 13 characterised in that a proximal end part (30) of the piston rod (12) has a smaller cross-section than other parts of the piston rod, in that the button (3) and the body (1) include relative locating means (31) which locate the proximal end part of the piston rod in line with the lip (7) of the end wall (6) without contact therewith and in that the relative locating means (31) include a recess in the body (1) nearer the end wall (6) than said abutment means (9) and a tooth (33–34) that prevents the button (3) from returning to the recess (31) after it has moved beyond said abutment means (9).

17. An aspirator syringe according to claim 13 characterised in that the button (3) and the body (1) include relative locating means (31) which locate the end of the skirt (15) of the piston (14) beyond the open end of the sleeve (4) or facing an internal recess in the sleeve and without contact therewith and in that the relative locating means (31) comprise a recess in the body (1) nearer the end wall (6) than said abutment means (9) and a tooth (33–34) that prevents the button (3) from returning to the recess (31) after it has moved beyond said abutment means (9).

18. An aspirator syringe according to claim 1 characterized in that the body (1) has at its proximal end beyond the end wall (6) an extension (8) which defines two diametrically opposed notches (10).

19. An aspirator device comprising:

an aspirator syringe (1–3) comprising three parts including (a) a plastic tubular body (1) defining over most of its length a sleeve (4) open at one end (5) and having an end wall (6) at the other end, said sleeve having a smooth inside wall, the end wall having a central orifice delimited by a convergent annular lip (7) directed axially towards the exterior of the sleeve, the body (1) having two holding lugs (11) projecting radially outwards, (b) a plastic piston rod/piston assembly (2) including a piston rod (12) that is solid or has no through conduit therein and that passes through the orifice in said end wall (6) and cooperates with the annular lip (7) to form a seal and a piston (14) at the distal end of the piston rod having a divergent peripheral skirt (15) directed towards the open end of the sleeve (4) and cooperating in sealed manner with said smooth inside wall of the sleeve, and (c) an actuator button (3) fixed to the proximal end of the piston rod (12); and at least one plastic nozzle (18) adapted to fit over or in and to be sealed to the open end of the sleeve (4) of the syringe, wherein the body (1) has an abutment (9) with which the button (3) comes into contact when the skirt (15) of the piston (14) is near the open end (5) of the sleeve (4) and is in contact with said smooth inside wall of the sleeve.

20. An aspirator device according to claim 19 characterised in that the nozzle (18) includes two aspirator conduits (19, 20) with different configurations and means (21; 25, 26) for selecting one or the other of said conduits.

21. An aspirator device according to claim 20 characterised in that the two conduits (19, 20) project from the distal end of the nozzle (18), at least one of the two conduits being adapted to be eliminated by means of a fragile area (21) connecting it to the remainder of the nozzle.

22. An aspirator device according to claim 20 characterised in that the two conduits (19, 20) project from respective opposite ends of the nozzle (18) which includes means (25, 26) adapted to fit over or into the open end (5) of the sleeve (4) in one direction or the other.

23. An aspirator device according to claim 20 wherein the at least one plastic nozzle comprises at least two interchangeable nozzles having different aspiration configurations.

* * * * *